US009474298B2

(12) United States Patent
Vanderhoof et al.

(10) Patent No.: US 9,474,298 B2
(45) Date of Patent: *Oct. 25, 2016

(54) PARTIALLY HYDROLYZED CASEIN-WHEY NUTRITIONAL COMPOSITIONS FOR REDUCING THE ONSET OF ALLERGIES

(75) Inventors: Jon A. Vanderhoof, Omaha, NE (US); Deolinda Scalabrin, Newburgh, IN (US)

(73) Assignee: Mead Johnson Nutrition Company, Glenview, IL (US)

(*) Notice: Subject to any disclaimer, the term of this patent is extended or adjusted under 35 U.S.C. 154(b) by 143 days.

This patent is subject to a terminal disclaimer.

(21) Appl. No.: 13/270,565

(22) Filed: Oct. 11, 2011

(65) Prior Publication Data

US 2013/0089572 A1    Apr. 11, 2013

(51) Int. Cl.

| | | |
|---|---|---|
| *A01N 63/00* | (2006.01) |
| *A61K 39/00* | (2006.01) |
| *A61K 39/38* | (2006.01) |
| *A61K 39/35* | (2006.01) |
| *A61K 39/36* | (2006.01) |
| *A23L 1/29* | (2006.01) |
| *A23L 1/305* | (2006.01) |
| *A23J 3/34* | (2006.01) |
| *A61K 38/01* | (2006.01) |
| *A61K 35/745* | (2015.01) |
| *A61K 35/747* | (2015.01) |

(52) U.S. Cl.
CPC ............... *A23L 1/296* (2013.01); *A23J 3/343* (2013.01); *A23L 1/3053* (2013.01); *A23L 1/3056* (2013.01); *A61K 35/745* (2013.01); *A61K 35/747* (2013.01); *A61K 38/018* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,670,268 A | 6/1987 | Mahmoud | |
| 5,032,399 A | 7/1991 | Gorbach et al. | |
| 5,374,567 A | 12/1994 | Cartagena | |
| 5,397,591 A | 3/1995 | Kyle et al. | |
| 5,550,156 A | 8/1996 | Kyle | |
| 7,618,669 B2 * | 11/2009 | Rangavajla et al. | 426/583 |
| 8,075,934 B2 * | 12/2011 | Banavara et al. | 426/72 |
| 8,137,718 B2 * | 3/2012 | Russell et al. | 426/61 |
| 2006/0286252 A1 | 12/2006 | Rangavajla et al. | |
| 2012/0172288 A1 * | 7/2012 | Wittke | A23L 1/296 514/2.5 |

FOREIGN PATENT DOCUMENTS

| | | |
|---|---|---|
| EP | 0631731 | 1/1995 |
| EP | 1264838 | 12/2002 |
| EP | 2436389 | 4/2012 |
| WO | 2006130200 | 12/2006 |
| WO | 2010079039 | 7/2010 |

OTHER PUBLICATIONS

Grummer-Strawn et al. 'Infant Feeding and Feeding Transitions During the First Year of Life.' Pediatrics 122:S36-S42, 2008.*
Colloff et al. 'Distribution and abundance of dust mites within homes.' Allergy 53(Suppl 48):24-27, 1998.*
Sporik et al. 'Exposure to house dust mite allergen (*Der p* 1) and the development of asthma in childhood.' N Engl J Med. 323:502-507, 1990.*
Halken, S. et al. "Comparison of a partially hydrolyzed infant formula with two extensively hydrolyzed formulas for allergy prevention: A prospective, randomized study," Pediatr Allergy Immunol. 2000: 11: 149-161.
Ling, J., et al. "Perspectives on Interactions Between Lactoferrin and Bacteria" Biochem Cell Biol. 84: 275-281 (2006).
Scalabrin, D., et al. "Growth and Tolerance of Healthy Term Infants Receiving Hydrolyzed Infant Formulas Supplemented With Lactobacillus rhamnosus GG: Randomized, Double-Blind, Controlled Trial," Clinical Pediatrics, vol. 48, No. 7, pp. 734-744, Sep. 2009.
Scalabrin, D., et al., "Infants Fed an Extensively Hydrolyzed Formula with Docosahexaenoic Acid (DHA), Arachidonic Acid (ARA), and Lactobacillus GG (LGG) Grow Normally." Abstract only. May 2008.
Scalabrin, D., et al., "Influence of Lactobacillus GG supplementation of partially and extensively hydrolyzed formulas on Infant long-chain polyunsaturated fatty acid status." Abstract only. 2008.
Scalabrin, D., et al., "Status of long-chain polyunsaturated fatty acids in infants receiving partially and extensively hydrolyzed formulas supplemented with Lactobacillus rhamnosus GG." Presented at: World Congress of Pediatric Gastroenterology, Hepatology and Nutrition; Aug. 20, 2008; Iguassu falls, Brazil. Abstract P0834.
Scholtens, P., et al., "Fecal Secretory Immunoglobulin A is Increased in Healthy Infants Who Receive a Formula with Short-Chain Galacto-Oligosaccharides and Long-Chain Fructo-Oligosaccharides1,2," J. Nutr. 138: 1141-1147 (2008).

(Continued)

*Primary Examiner* — Nora Rooney
(74) *Attorney, Agent, or Firm* — Patterson Intellectual Property Law, P.C.; James R. Cartiglia; Bethany J. Whelan

(57) ABSTRACT

The present disclosure relates to methods of reducing the onset of allergies. In certain embodiments, the method includes administering to an infant a nutritional composition that includes a fat or lipid source, a carbohydrate source, a protein source comprising whey and casein proteins and, optionally, a probiotic. In certain embodiments, the whey:casein ratio in the protein source is from about 50:50 to about 70:30 and the degree of hydrolysis of the proteins included in the protein source is from about 4% to about 10%.

20 Claims, No Drawings

(56) References Cited

OTHER PUBLICATIONS

Von Berg, A., et al., "The effect of hydrolyzed cow's milk formula for allergy prevention in the first year of life: The German Infant Nutritional Intervention Study, a randomized double-blind trial," J. Allergy Clin Immunol. vol. 111, No. 3, pp. 533-540, Mar. 2003.

Lee, Y-H., "Food-processing approaches to altering allergenic potential of milk-based formula," Journal of Pediatrics, vol. 121, No. 5, Part 02, Nov. 1, 1992.

Mahmoud, M.I., et al., "Enzymatic Hydrolysis of Casein: Effect of degree of hydrolysis on antigenicity and physical properties," Journal of Food Science, vol. 57, No. 5, Sep. 1, 1992.

* cited by examiner

PARTIALLY HYDROLYZED CASEIN-WHEY NUTRITIONAL COMPOSITIONS FOR REDUCING THE ONSET OF ALLERGIES

BACKGROUND

1. Technical Field

This disclosure relates generally to the field of nutritional compositions, such as infant formulas, human milk fortifiers, children's dietary supplements, and the like, that contain a fat or lipid source, a carbohydrate source, and a protein source comprising whey and casein proteins as well as to methods of administering such compositions.

2. Background

Children and infants are susceptible to a number of different allergies, including, without limitation, allergic colititis, allergic enterocolitis, allergic esophagatis, allergic gastroesophagitis, allergic urticaria, atopic dermatitis, allergic reactions to cow's milk, allergic reactions to egg, allergic reactions to soy, allergic reactions to house dust, allergic reactions to mites, and gut inflammation. Allergies can lead to a number of adverse health events, including trouble breathing and even death in particularly vulnerable children and infants. Thus, it is particularly important that nutritional compositions for children and infants be formulated so as to reduce the onset of allergies.

Accordingly, it is an object of the present disclosure to provide nutritional compositions for children and infants that reduce the onset of allergies.

In addition, nutritional compositions containing high levels of lactose can cause a variety of symptoms, such as abdominal bloating, gas, cramps and diarrhea, in infants and children that do not produce sufficient amounts of the enzyme lactase. Thus, in certain embodiments, the nutritional compositions of the present disclosure have a low level of lactose.

BRIEF SUMMARY

Briefly, the present disclosure is directed, in an embodiment, to a method of reducing the onset of allergies in a human, such as a child or infant.

In one embodiment, the present disclosure provides a method of reducing the onset of allergies in a human comprising administering to a human, when the human is an infant, a nutritional composition including:
  a. a fat or lipid source;
  b. a protein source; and
  c. a carbohydrate source.

In certain embodiments, the protein source of the nutritional compositions comprises whey and casein proteins and the whey and casein proteins are partially hydrolyzed. Preferably, the weight ratio of whey to casein proteins is, for example, from about 50:50 to about 70:30, more preferably about 60:40, and the degree of hydrolysis of the whey and casein proteins included in the protein source is from about 4% to about 10%, more preferably about 6% to about 9%.

Preferably, the nutritional composition is a nutritionally complete composition. In particular embodiments, the nutritional composition is a weaning formula. Preferably, the nutritional composition is administered to an infant who has a family history of allergies as a method of reducing the onset of allergic manifestations when the infant becomes a child of about 2 years of age or older. Preferably, the infant is at risk of developing one or more allergic manifestations in childhood. In certain embodiments, the allergic manifestations include allergic colititis, allergic enterocolitis, allergic esophagatis, allergic gastroesophagitis, allergic urticaria, atopic dermatitis, allergic reactions to cow's milk, allergic reactions to egg, allergic reactions to soy, allergic reactions to house dust, allergic reactions to mites, gut inflammation, and combinations thereof. It is also preferred that the administration of the nutritional composition increases the concentration of fecal secretory IgA (sIgA) in the human.

Preferably, the nutritional composition comprises a probiotic source. In certain embodiments, the probiotic source comprises *Lactobacillus rhamnosus* GG and *Lactobacillus rhamnosus* GG is present in the nutritional composition in an amount such that the human is administered between about $10^4$ to about $10^{10}$ colony forming units (cfu) per kg body weight per day. In certain embodiments, the nutritional composition comprises between about_to about_cfu of *Lactobacillus rhamnosus* GG per 100 kcal.

In certain embodiments, the carbohydrate source comprises between about 15% to about 55%, more preferably between about 20% and about 30%, lactose, by weight. The carbohydrate source may further comprise about 0.1 g/100 kcal to about 1 g/100 kcal of a prebiotic composition. More preferably, the carbohydrate source comprises about 0.1 g/100 kcal to about 1 g/100 kcal of a prebiotic composition which comprises a combination of polydextrose and galactooligosaccharide.

In certain embodiments, the whey and casein proteins in the protein source have the molecular weight distribution set forth in Table 1.

TABLE 1

| Molar Mass (in Daltons) | % Molecular Weight Distribution |
|---|---|
| <500 | 11-20 |
| 500-1000 | 25-38 |
| 1000-2000 | 27-30 |
| 2000-3000 | 8-16 |
| 3000-5000 | 3-10 |
| >5000 | 2-11 |

It is especially preferred that the whey and casein proteins in the protein source have the molecular weight distribution set forth in Table 2.

TABLE 2

| Molar Mass (in Daltons) | % Molecular Weight Distribution |
|---|---|
| <500 | 17 |
| 500-1000 | 35.1 |
| 1000-2000 | 30.9 |
| 2000-3000 | 9.6 |
| 3000-5000 | 4.2 |
| >5000 | 2.8 |

DETAILED DESCRIPTION

In one embodiment, the present disclosure provides a method of reducing the onset of allergies in a human comprising administering to the human, when the human is an infant, a nutritional composition including a fat or lipid source, a carbohydrate source, and a protein source comprising partially hydrolyzed whey and casein proteins.

In an embodiment, the nutritional composition is administered to an infant as a method of reducing the onset of allergic manifestations when the infant becomes a child of about 2 years of age or older. As used herein, "a child" and "children" mean humans over the age of about 12 months to about 12 years old. The term "infant" is generally defined as a human from about birth to about 12 months of age. A "full term infant" as used herein means an infant born after at least about 37 weeks gestation, while a "preterm infant" is an infant born after less than about 37 weeks gestation.

Preferably, the infant has a family history of allergies and is at risk of developing one or more allergic manifestations in childhood. In certain embodiments, the allergic manifestations include allergic colitis, allergic enterocolitis, allergic esophagatis, allergic gastroesophagitis, allergic urticaria, atopic dermatitis, allergic reactions to cow's milk, allergic reactions to egg, allergic reactions to soy, allergic reactions to house dust, allergic reactions to mites, gut inflammation, and combinations thereof.

It is also preferred that the administration of the nutritional composition results in a higher level of fecal secretory IgA (sIgA). sIgA is produced by activated B-cells in the mucosa where it forms immune complexes with pathogens and allergens, thereby preventing them from binding to and penetrating the intestinal mucosa. Persons with low IgA levels have increased risk of infections in mucosal surfaces, and food allergies. Thus, increasing the level of sIgA may reduce the onset of allergies.

The whey and casein proteins for use in the nutritional compositions may be any form of whey and casein proteins, including but not limited to milk protein concentrates, milk protein isolates, non-fat dry milk, milk protein powders, skim milk powders, whole milk powders, whey protein isolates, whey protein concentrates, sweet whey, acid whey, acid casein and caseinate (e.g. sodium caseinate, sodium calcium caseinate, calcium caseinate) and any combinations thereof. Thus, as used herein, the terms "whey" and "whey proteins" refers to any form of whey protein and the terms "casein" and "casein proteins" refers to any form of casein protein. In a particular embodiment, the source of whey and casein proteins in the nutritional composition comprise partially hydrolyzed non-fat milk powder, partially hydrolyzed whey protein concentrate, milk protein partial hydrolysates or any combination thereof.

In an embodiment, the ratio of whey proteins to casein proteins in the protein source is from about 50:50 to about 70:30, more preferably about 60:40.

In a particular embodiment, the composition of the disclosure is a reduced-lactose, partially-hydrolyzed protein, milk-based nutritional composition which provides physiochemical and physiological benefits, such as supporting the resistance to the onset of allergies.

In certain embodiments, the degree of hydrolysis of the whey and casein proteins included in the protein source is from about 4% to about 10%, more preferably about 6% to about 9%. "Degree of hydrolysis" as used herein means the extent to which peptide bonds are broken by an enzymatic hydrolysis reaction. The measurement shows the number of specific peptide bonds broken in hydrolysis as a percent of the total number of specific peptide bonds present in the intact protein.

In one embodiment, the casein and whey proteins included in the protein source have the molecular weight distribution shown in Table 1. In another embodiment, the casein and whey proteins included in the protein source have the molecular weight distribution shown in Table 2.

In certain embodiments the nutritional composition is a weaning formula, administered as the mother is weaning the infant from the breast to other foods.

In some embodiments, the nutritional composition may be an infant formula. The term "infant formula" applies to a composition in liquid or powdered form that satisfies the nutrient requirements of an infant by being a substitute for human milk. In the United States, the content of an infant formula is dictated by the federal regulations set forth at 21 C.F.R. §§100, 106 and 107. These regulations define macronutrient, vitamin, mineral, and other ingredient levels in an effort to simulate the nutritional and other properties of human breast milk. In a separate embodiment, the nutritional composition may be a human milk fortifier, meaning it is a composition which is added to human milk in order to enhance the nutritional value of human milk. As a human milk fortifier, the disclosed composition may be in powder or liquid form. In yet another embodiment, the disclosed nutritional composition may be a children's nutritional composition.

The nutritional compositions of the disclosure may provide minimal, partial, or total nutritional support. The nutritional compositions may be nutritional supplements or meal replacements. In some embodiments, the nutritional compositions may be administered in conjunction with a food or another nutritional composition. In this embodiment, the nutritional compositions can either be intermixed with the food or other nutritional composition prior to ingestion by the subject or can be administered to the subject either before or after ingestion of a food or nutritional composition. The nutritional compositions may be administered to preterm infants receiving infant formula, breast milk, a human milk fortifier, or combinations thereof.

The nutritional compositions may, but need not, be nutritionally complete. The skilled artisan will recognize "nutritionally complete" to vary depending on a number of factors including, but not limited to, age, clinical condition, and dietary intake of the subject to whom the term is being applied. In general, "nutritionally complete" means that the nutritional composition of the present disclosure provides adequate amounts of all carbohydrates, lipids, essential fatty acids, proteins, essential amino acids, conditionally essential amino acids, vitamins, minerals, and energy required for normal growth. As applied to nutrients, the term "essential" refers to any nutrient which cannot be synthesized by the body in amounts sufficient for normal growth and to maintain health and which therefore must be supplied by the diet. The term "conditionally essential" as applied to nutrients means that the nutrient must be supplied by the diet under conditions when adequate amounts of the precursor compound is unavailable to the body for endogenous synthesis to occur.

The composition which is "nutritionally complete" for the preterm infant will, by definition, provide qualitatively and quantitatively adequate amounts of all carbohydrates, lipids, essential fatty acids, proteins, essential amino acids, conditionally essential amino acids, vitamins, minerals, and energy required for growth of the preterm infant. The composition which is "nutritionally complete" for the full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant. The composition which is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

The nutritional composition may be provided in any form known in the art, including a powder, a gel, a suspension, a paste, a solid, a liquid, a liquid concentrate, or a ready-to-use product.

In the preferred embodiments, the nutritional composition disclosed herein may be administered enterally. As used herein, "enteral" means through or within the gastrointestinal, or digestive, tract, and "enteral administration" includes oral feeding, intragastric feeding, transpyloric administration, or any other introduction into the digestive tract.

In an embodiment, the nutritional composition comprises:
a. up to about 7 g/100 kcal of a fat or lipid source, more preferably from about 3 g/100 kcal to about 7 g/100 kcal of a fat or lipid source;
b. up to about 5 g/100 kcal of a protein source, more preferably from about 1 g/100 kcal to about 5 g/100 kcal of a protein source; and
c. up to about 12 g/100 kcal of a carbohydrate source, more preferably from about 8 g/100 kcal to about 12 g/100 kcal of a carbohydrate source.

Suitable fat or lipid sources for practicing the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In an embodiment of the present disclosure, the carbohydrate source comprises between about 15% and about 55% lactose, by weight. In yet another embodiment of the present disclosure, the carbohydrate source comprises between about 20% and about 30% lactose, by weight. In these embodiments, the remaining source of carbohydrates may be any carbohydrate source known in the art, including but not limited to, glucose, corn syrup solids, maltodextrins, sucrose, starch, rice syrup solids, rice starch, and the like.

The nutritional compositions of the present disclosure, in certain embodiments, may further comprise a probiotic. A "probiotic" is a microorganism with low or no pathogenicity that exerts beneficial effects on the health of the host.

In a particular embodiment, the probiotic may be selected from *Lactobacillus* species, *Lactobacillus rhamnosus* GG, *Bifidobacterium* species, *Bifidobacterium longum*, and *Bifidobacterium animalis* subsp. *lactis* BB-12. In an especially preferred embodiment, the nutritional compositions comprise *Lactobacillus rhamnosus* GG ("LGG").

LGG is a probiotic strain isolated from healthy human intestinal flora. It was disclosed in U.S. Pat. No. 5,032,399 to Gorbach, et al, which is herein incorporated in its entirety, by reference thereto. LGG is resistant to most antibiotics, stable in the presence of acid and bile, and attaches avidly to mucosal cells of the human intestinal tract. It survives for 1-3 days in most individuals and up to 7 days in 30% of subjects. In addition to its colonization ability, LGG also beneficially affects mucosal immune responses. LGG is deposited with the depository authority American Type Culture Collection under accession number ATCC 53103.

The amount of the *Lactobacillus rhamnosus* GG in the nutritional compositions may vary. In one embodiment, the compositions contain an amount of *Lactobacillus rhamnosus* GG such that the amount of *Lactobacillus rhamnosus* GG administered ranges from about $10^4$ to about $10^{10}$ cfu per kg body weight per day. In another embodiment, the amount of the *Lactobacillus rhamnosus* GG may vary from about $10^6$ to about $10^9$ cfu per kg body weight per day. In yet another embodiment, the amount of the *Lactobacillus rhamnosus* GG may be at least about $10^6$ cfu per kg body weight per day. Preferably, the nutritional compositions comprise from about_to about_cfu per 100 kcal of *Lactobacillus rhamnosus* GG.

In addition to *Lactobacillus rhamnosus* GG or instead of *Lactobacillus rhamnosus* GG, the nutritional composition may contain other probiotics. Any probiotic known in the art may be acceptable in this embodiment provided it achieves the intended result. In a particular embodiment, the probiotic may be selected from other *Lactobacillus* species, *Bifidobacterium* species, *Bifidobacterium longum*, and *Bifidobacterium animalis* subsp. *lactis* BB-12. Such probiotics may be naturally-occurring, synthetic or developed through the genetic manipulation of organisms, whether such new source is now known or later developed.

In an embodiment, one or more of the probiotics included in the nutritional compositions is viable. In another embodiment, one or more of the probiotics is non-viable. As used herein, the term "viable" refers to live microorganisms. The term "non-viable" or "non-viable probiotic" means non-living probiotic microorganisms, their cellular components and metabolites thereof. Such non-viable probiotics may have been heat-killed or otherwise inactivated but retain the ability to favorably influence the health of the host. Preferably, the probiotic is viable. In certain embodiments, the probiotic is present in the nutritional composition in an amount such that the human is administered between about $10^4$ to about $10^{10}$ cfu per kg body weight per day. In certain embodiments, the nutritional composition comprises between about_to about_cfu of probiotics per 100 kcal.

In one embodiment of the disclosure, the nutritional compositions may include a prebiotic composition comprising one or more prebiotics. As used herein, the term "prebiotic" means a non-digestible food ingredient that beneficially affects the host by selectively stimulating the growth and/or activity of one or a limited number of bacteria in the colon that can improve the health of the host. A "prebiotic composition" is a composition that comprises one or more prebiotics. Such prebiotics may be naturally-occurring, synthetic, or developed through the genetic manipulation of organisms and/or plants, whether such new source is now known or developed later.

Prebiotics useful in the present disclosure may include oligosaccharides, polysaccharides, and other prebiotics that contain fructose, xylose, soya, galactose, glucose and mannose. More specifically, prebiotics useful in the present disclosure may include lactulose, lactosucrose, raffinose, gluco-oligosaccharide, inulin, polydextrose, polydextrose powder, galactooligosaccharide, fructo-oligosaccharide, isomalto-oligosaccharide, soybean oligosaccharides, lactosucrose, xylo-oligosacchairde, chito-oligosaccharide, manno-oligosaccharide, aribino-oligosaccharide, siallyl-oligosaccharide, fuco-oligosaccharide, and gentio-oligosaccharides. Preferably, the nutritional compositions comprise polydextrose and/or galactooligosaccaharide. Optionally, in addition to polydextrose and/or galactooligosaccaharide, the nutritional compositions comprise one or more additional prebiotics.

If included in the nutritional compositions, the total amount of prebiotics present in the nutritional composition may be from about 0.1 g/100 kcal to about 1 g/100 kcal. More preferably, the total amount of prebiotics present in the nutritional composition may be from about 0.3 g/100 kcal to about 0.7 g/100 kcal. At least 20% of the prebiotics should comprise galactooligosaccharide and/or polydextrose.

If polydextrose is used in the prebiotic composition, the amount of polydextrose in the nutritional composition may, in an embodiment, be within the range of from about 0.1 g/100 kcal to about 1.0 g/100 kcal. In another embodiment, the amount of polydextrose is within the range of from about 0.2 g/100 kcal to about 0.6 g/100 kcal.

If galactooligosaccharide is used in the prebiotic composition, the amount of galactooligosaccharide in the nutritional composition may, in an embodiment, be from about 0.1 g/100 kcal to about 1.0 g/100 kcal. In another embodiment, the amount of galactooligosaccharide in the nutritional composition may be from about 0.2 g/100 kcal to about 0.5 g/100 kcal. In certain embodiments, the ratio of polydextrose to galactooligosaccharide in the prebiotic composition is between about 9:1 and about 1:9.

The nutritional formulation of the disclosure, in some embodiments, may further contain a source of long chain polyunsaturated fatty acids (LCPUFAs). Preferably, the source of LCPUFAs comprises docosahexanoic acid (DHA). Other suitable LCPUFAs include, but are not limited to, α-linoleic acid, γ-linoleic acid, linoleic acid, linolenic acid, eicosapentanoic acid (EPA) and arachidonic acid (ARA).

In one embodiment, the nutritional composition is supplemented with both DHA and ARA. In this embodiment, the weight ratio of ARA:DHA may be from about 1:3 to about 9:1. In one embodiment of the present disclosure, the weight ratio of ARA:DHA is from about 1:2 to about 4:1. In another embodiment, the weight ratio of ARA:DHA is from about 2:3 to about 2:1.

The amount of long chain polyunsaturated fatty acids in the nutritional composition may vary from about 5 mg/100 kcal to about 100 mg/100 kcal, more preferably from about 10 mg/100 kcal to about 50 mg/100 kcal. For example, the nutritional compositions may include from about 15 mg/100 kcal to about 20 mg/100 kcal DHA and from about 20 mg/100 kcal to about 40 mg/100 kcal, ARA.

The nutritional composition may be supplemented with oils containing DHA and ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and ARA may be any source known in the art such as marine oil, fish oil, single cell oil, egg yolk lipid, and brain lipid. In some embodiments, the DHA and ARA are sourced from the single cell Martek oil, DHASCO®, or variations thereof. The DHA and ARA can be in natural form, provided that the remainder of the LCPUFA source does not result in any substantial deleterious effect on the infant or child. Alternatively, the DHA and ARA can be used in refined form.

In an embodiment of the present disclosure, sources of DHA and ARA are single cell oils as taught in U.S. Pat. Nos. 5,374,567; 5,550,156; and 5,397,591, the disclosures of which are incorporated herein in their entirety by reference thereto. However, the present disclosure is not limited to only such oils.

The nutritional composition of the disclosure also includes lactoferrin in some embodiments. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pl 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR), herein SEQ ID. No.: 1 and 28 to 31 (RKVR), herein SEQ ID. No.: 2 are arginine-rich cationic domains in the N-terminus especially critical to the antimicrobial activities of lactoferrin. A similar region in the N-terminus is found in bovine lactoferrin (residues 17 to 42; FKCRRWQWRMKKLGAPSITCVR-RAFA) herein SEQ. ID. NO.: 3.

As described in "*Perspectives on Interactions Between Lactoferrin and Bacteria*" which appeared in the publication BIOCHEMISTRY AND CELL BIOLOGY, pp 275-281 (2006), lactoferrins from different host species may vary in their amino acid sequences though commonly possess a relatively high isoelectric point with positively charged amino acids at the end terminal region of the internal lobe. Suitable lactoferrins for use in the present disclosure include those having at least 48% homology with the amino acid sequence AVGEQEL-RKCNQWSGL, herein SEQ. ID. NO.: 4, at the HLf (349-364) fragment. For example, suitable lactoferrins include, without limitation, human lactoferrin, bovine lactoferrin, porcine lactoferrin, equine lactoferrin, buffalo lactoferrin, goat lactoferrin, murine lactoferrin and camel lactoferrin.

In a preferred embodiment, the lactoferrin is lactoferrin obtained from a non-human source. As used herein, "lactoferrin obtained from a non-human source" means lactoferrin which is from a source other than human breast milk. For example, in certain embodiments, the lactoferrin is human lactoferrin produced by a genetically modified organism and/or non-human lactoferrin. The term "non-human lactoferrin", as used herein, refers to lactoferrin having an amino acid sequence that is different than the amino acid sequence of human lactoferrin.

In one embodiment, lactoferrin is present in the nutritional compositions in an amount of from about 70 mg/100 kcal to about 220 mg/100 kcal; in another embodiment, lactoferrin is present in an amount of about 90 mg/100 kcal to about 190 mg/100 kcal.

In addition, the nutritional composition of the disclosure may also contain TGF-β.

In a particular embodiment of the disclosure, the level of TGF-β in the disclosed composition is from about 0.0150 (pg/μg) ppm to about 0.1000 (pg/μg) ppm. In another embodiment, the level of TGF-β in the disclosed composition is from about 0.0225 (pg/μg) ppm to about 0.0750 (pg/μg) ppm.

In a particular embodiment of the disclosure, the level of TGF-β in the disclosed composition is from about 2500 pg/mL to about 10,000 pg/mL composition, more preferably from about 3000 pg/mL to about 8000 pg/mL.

In one embodiment, the ratio of TGF-β1:TGF-β2 in the disclosed composition is in the range of about 1:1 to about 1:20, or, more particularly, in the range of about 1:5 to about 1:15.

In some embodiments, the composition of the disclosure induces oral tolerance. As used herein, the term "oral tolerance" refers to the specific suppression of cellular and/or humoral immune responses to an antigen by prior administration of the antigen by the oral route. Oral tolerance affects the responsiveness of the local immune system in the intestinal mucosa itself, thus preventing hypersensitivity reactions to food proteins that could otherwise elicit potent inflammatory reactions in the gut. Development of oral tolerance is an important component in appropriate mucosal immune function. Oral antigens, like food or commensal bacteria, are normally processed in a manner that results in a regulated immune response. This response does not injure the host and results in systemic hypo-responsiveness in subsequent oral challenge with the same food antigen. Thus oral tolerance is established. Oral tolerance can fail, however, in response to the development and pathogenesis of several immunologically based diseases, including inflammatory bowel disease, Crohn's disease, and ulcerative colitis. In a particular embodiment, the combination of TGF-β and prebiotics may synergistically contribute to the induction of oral tolerance to antigens in circumstances where oral tolerance has previously failed. In some embodiments, the induction of oral tolerance may be enhanced by administration of the composition of the disclosure. In other embodiments, the oral tolerance acquired by a subject may be maintained by administration of the composition of the disclosure.

EXAMPLES

The following examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

Example 1

This example illustrates a nutritional composition, in powder form, prepared according to an embodiment of the present disclosure.

| | |
|---|---|
| *Lactobacillus* GG | 1 × 10$^{12}$ CFU |
| Powder Base | 87.00 kg |
| Corn Syrup Solids | (32.229 kg) |
| Partially Hydrolyzed NFM & WPC | (26.865 kg) |
| Fat Blend, bulk | (26.187 kg) |
| Palm Olein Oil | (11.785 kg) |
| Soybean Oil | (5.237 kg) |
| Coconut Oil | (5.237 kg) |
| High Oleic Sunflower Oil | (3.928 kg) |
| Single Cell ARA & DHA Oil Blend (0.457 kg single cell arachidonic acid oil; 0.229 kg single cell docosahexaenoic acid oil) | 0.686 kg |
| Calcium Carbonate | 0.400 kg |
| Calcium Phosphate (Tribasic) | 0.200 kg |
| Potassium Chloride | 0.200 kg |
| Choline Chloride | 0.134 kg |
| Magnesium Phosphate, Dibasic | 0.100 kg |
| Sodium Citrate Dihydrate | 10.005 g |
| L-Carnitine | 9.570 g |
| Corn Syrup Solids, Restricted Sodium | 12.271 kg |
| Premix Dry Vitamin | 0.321 kg |
| Ascorbic Acid | (156.687 g) |
| Inositol | (39.887 g) |
| Corn Syrup Solids | (35.478 g) |
| Taurine | (33.875 g) |
| Dry Vitamin E Acetate | (25.279 g) |
| Vitamin A Palmitate | (7.871 g) |
| Niacinamide | (6.475 g) |
| Vitamin K$_1$ | (5.454 g) |
| Calcium Pantothenate | (3.299 g) |
| Vitamin B$_{12}$ | (2.122 g) |
| Biotin Trituration 1% | (1.608 g) |
| Vitamin D$_3$ Powder | (0.969 g) |
| Riboflavin | (0.755 g) |
| Thiamin Hydrochloride | (0.601 g) |
| Pyridoxine Hydrochloride | (0.518 g) |
| Folic Acid | (0.122 g) |
| Iron Trituration | 0.248 kg |
| Corn Syrup Solids | (192.187 g) |
| Ferrous Sulfate, Heptahydrate | (49.60 g) |
| Ascorbic Acid | (6.213 g) |
| Trace/Ultra-Mineral Premix | 0.160 kg |
| Lactose, Grind A | (138.017 g) |
| Zinc Sulfate, Monohydrate | (16.422 g) |
| Sodium Selenite | (3.634 g) |
| Cupric Sulfate Powder | (1.688 g) |
| Manganese Sulfate, Monohydrate | (0.239 g) |
| Water, defluoridated | 0.21 kg |

The nutritional composition can be reconstituted in liquid form, by for example, adding 19.46 gram of powder to 133 ml of water. Preferably, the nutritional composition is administered to a child or infant and reduces the onset of allergies in the child or infant.

Example 2

This example illustrates a nutritional composition, the form of a ready-to-use liquid, prepared according to an embodiment of the present disclosure.

| | |
|---|---|
| *Lactobacillus* GG | 1 × 10$^{11}$ CFU |
| De-Flouridated Water | 8972.706 LT |
| Corn Syrup Solids 25 DE Low Sodium | 459.978 kg |
| Milk Protein Partial Hydrolysate | 366.864 kg |
| Fat Blend | 329.800 kg |
| Waxy Rice Starch | 136.166 kg |
| DATEM Emulsifier | 22.640 kg |
| Fungal-Algal Oil Blend | 9.365 kg |
| Calcium Carbonate Hi Density | 4.372 kg |
| Premix Dry Vitamin | 4.260 kg |
| Ascorbic Acid | (2.710 kg) |
| Taurine | (0.588 kg) |
| Inositol | (0.487 kg) |
| Corn Syrup Solids | (0.213 kg) |
| Niacinamide | (85.456 g) |
| Potassium iodide titration (47.952 g corn syrup; 0.484 g potassium iodide) | (48.436 g) |
| Calcium Pantothenate Powder | (44.773 g) |
| Biotin Trituration 1% | (27.051 g) |
| Vitamin B12 0.1% in Starch | (23.813 g) |
| Riboflavin FCC | (12.737 g) |
| Thiamine HCL Crystalline Powder | (10.394 g) |
| Pyridoxine Hydrochloride FCC | (7.114 g) |
| Folic Acid Fine Powder | (2.002 g) |
| Calcium Phosphate Tribasic Ultrafine | 2.719 kg |
| Choline Chloride Powder | 2.086 kg |
| Magnesium Chloride | 1.765 kg |
| Ferrous Sulfate Heptahydrate | 0.658 kg |
| Antifoam 1520 | 0.516 kg |

-continued

| | |
|---|---|
| L-Carnitine | 132.00 g |
| Sodium Citrate | 15.00 g |
| Fat-Soluble Vitamin PreMix | 0.323 kg |
| Soy oil | (141.251 g) |
| Tocopheryl Acetate DL-Alpha | (0.160 kg) |
| Vitamin A Palmitate | (14.567 g) |
| Cholecalciferol Concentrate | (5.992 g) |
| Vitamin K Phytonadione Liquid | (0.804 g) |
| Trace/Ultra-Mineral Premix | 0.317 kg |
| Lactose, Grind A | (26.669 g) |
| Zinc Sulfate, Monohydrate | (0.192 kg) |
| Sodium Selenite anhydrous | (0.349 g) |
| Sodium Selenite in Corn Syrup Solids, spray dried trituration | (69.718 g) |
| Cupric Sulfate Powder | (24.431 g) |
| Manganese Sulfate, Monohydrate | (4.137 g) |
| Corn syrup solids | (69.369 g) |

Preferably, the nutritional composition is administered to a child or infant and reduces the onset of allergies in the child or infant.

Example 3

This example illustrates a nutritional composition, in the form of a liquid nursette, prepared according to an embodiment of the present disclosure.

| | |
|---|---|
| *Lactobacillus* GG | 1 × 10$^{11}$ CFU |
| De-Flouridated Water | 8971.753 LT |
| Corn Syrup Solids 25 DE Low Sodium | 441.663 kg |
| Milk Protein Partial Hydrolysate | 366.864 kg |
| Fat Blend | 329.800 kg |
| Waxy Rice Starch | 152.668 kg |
| DATEM Emulsifier | 21.508 kg |
| Fungal-Algal Oil Blend | 9.365 kg |
| Calcium Carbonate Hi Density | 4.642 kg |
| Premix Dry Vitamin | 4.260 kg |
| Ascorbic Acid | (2.710 kg) |
| Taurine | (0.588 kg) |
| Inositol | (0.487 kg) |
| Corn Syrup Solids | (0.213 kg) |
| Niacinamide | (85.456 g) |
| Potassium iodide titration (47.952 g corn syrup; 0.484 g potassium iodide) | (48.436 g) |
| Calcium Pantothenate Powder | (44.773 g) |
| Biotin Trituration 1% | (27.051 g) |
| Vitamin B12 0.1% in Starch | (23.813 g) |
| Riboflavin FCC | (12.737 g) |
| Thiamine HCL Crystalline Powder | (10.394 g) |
| Pyridoxine Hydrochloride FCC | (7.114 g) |
| Folic Acid Fine Powder | (2.002 g) |
| Calcium Phosphate Tribasic Ultrafine | 3.473 kg |
| Ascorbic acid | 2.711 kg |
| Choline Chloride Powder | 2.086 kg |
| Magnesium Chloride | 1.765 kg |
| Ferrous Sulfate Heptahydrate | 0.657 kg |
| Antifoam 1520 | 0.516 kg |
| L-Carnitine | 132.00 g |
| Sodium Citrate | 26 g |
| Fat-Soluble Vitamin PreMix | 0.323 kg |
| Soy oil | (141.251 g) |
| Tocopheryl Acetate DL-Alpha | (0.160 kg) |
| Vitamin A Palmitate | (14.567 g) |
| Cholecalciferol Concentrate | (5.992 g) |
| Vitamin K Phytonadione Liquid | (0.804 g) |
| Trace/Ultra-Mineral Premix | 0.317 kg |
| Lactose, Grind A | (26.669 g) |
| Zinc Sulfate, Monohydrate | (0.192 kg) |
| Sodium Selenite anhydrous | (0.349 g) |
| Sodium Selenite in Corn Syrup Solids, spray dried trituration | (69.718 g) |
| Cupric Sulfate Powder | (24.431 g) |
| Manganese Sulfate, Monohydrate | (4.137 g) |
| Corn syrup solids | (69.369 g) |

Preferably, the nutritional composition is administered to a child or infant and reduces the onset of allergies in the child or infant.

Example 4

This example provides nutritional information for the compositions described in Examples 1-3.

| | Per 100 kcal (5 fl. oz) (Examples 2 and 3) | Per 100 g Powder (510 kcal) (Example 1) |
|---|---|---|
| Protein, g | 2.3 | 11.8 |
| Fat, g | 5.3 | 27 |
| Linoleic acid, mg | 860 | 4400 |
| Linolenic acid, mg | 80 | 410 |
| DHA, mg | 17 | 87 |
| ARA, mg | 34 | 175 |
| Carbohydrate, g | 10.8 | 56 |
| Lactose, g | 2.5 | 13 |
| Water, g | | |
| Powder | 134 | 2.6 |
| Liquid | 133 | |
| Vitamins/Other Nutrients | | |
| Vitamin A, IU | 300 | 1540 |
| Vitamin D, IU | 60 | 310 |
| Vitamin E, IU | 2 | 10.3 |
| Vitamin K, mcg | 9 | 46 |
| Thiamin, mcg | 80 | 410 |
| Riboflavin, mcg | 140 | 720 |
| Vitamin B$_6$, mcg | 60 | 310 |
| Vitamin B$_{12}$, mcg | 0.3 | 1.54 |
| Niacin, mcg | 1000 | 5100 |
| Folic Acid, mcg | 16 | 82 |
| Pantothenic Acid, mcg | 500 | 2600 |
| Biotin, mcg | 3 | 15.4 |
| Vitamin C, mg | 12 | 62 |
| Choline, mg | 24 | 123 |
| Inositol, mg | 6 | 31 |
| Carnitine, mg | 2 | 10.3 |
| Taurine, mg | 6 | 31 |
| Minerals | | |
| Calcium, mg | 82 | 420 |
| Phosphorus, mg | 46 | 240 |
| Magnesium, mg | 8 | 41 |
| Iron, mg | 1.8 | 9.3 |
| Zinc, mg | 1 | 5.1 |
| Manganese, mcg | 15 | 77 |
| Copper, mcg | 75 | 390 |
| Iodine, mcg | 15 | 77 |
| Selenium, mcg | 2.8 | 14.4 |
| Sodium, mg | 36 | 185 |
| Potassium, mg | 108 | 560 |
| Chloride, mg | 63 | 320 |

Example 5

This example illustrates the use of a nutritional composition according to an embodiment of the present disclosure.

Infants at high risk of allergy are randomly assigned before or at birth to receive a control formula or an experimental formula when they wean from breast milk for any reason, either a need for breast milk partial supplementation or complete replacement until 6 months of age. The control formula is Enfamil Lipil® (Mead Johnson Nutrition). The experimental formula is a formula prepared according to any one of Examples 1-3 above. The participants are followed up to 2 years of age. The primary outcome is a marker of gut inflammation (fecal calprotecitin) and sensitization to the main allergens (as measured by total serum IgE as well as specific IgE to cow's milk, egg, soy, and house dust mites), measured at the end of the first year of life. Secondary outcomes include the presence of allergic manifestations, such as atopic dermatitis (measured through diagnosis and severity assessment through SCORAD), gastrointestinal manifestation of food allergy (e.g., allergic colitis, allergic enterocolitis, allergic esophagatis, allergic gastroesophagitis, and/or allergic uticaria) and incidence of infections diseases throughout the first 2 years of life. Fecal secretory IgA as well as a number of comfort/tolerance criteria will be monitored (e.g., stool number and consistency, gas, fussiness and irritability, and formula acceptance). Inclusion criteria for the study include healthy term infants having history of allergy in both parents or one parent and a sibling.

Preferably, the nutritional composition of Examples 1-3 reduces the onset of allergies as compared to the control.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although preferred embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged both in whole or in part. For example, while methods for the production of a commercially sterile liquid nutritional supplement made according to those methods have been exemplified, other uses are contemplated. Therefore, the spirit and scope of the appended claims should not be limited to the description of the preferred versions contained therein.

What is claimed is:

1. A method of increasing the concentration of fecal secretory IgA in a child having an allergic reaction to at least one antigen, wherein the child is at least two years of age or older, the method comprising the steps of:
   exposing the child, when the child is an infant, to the at least one antigen, wherein the at least one antigen is selected from the group consisting of cow's milk, egg, soy, house dust, and mites; and
   administering to the child, when the child is an infant, a nutritional composition comprising from 3 g/100 kcal to 7 g/100 kcal of a fat or lipid source; from 8 g/100 kcal to 12 g/100 kcal of a carbohydrate source, wherein the carbohydrate source comprises between 15% and 55% lactose by weight; a probiotic source comprising *Lactobacillus rhamnosus* GG; a non-human lactoferrin; a prebiotic source comprising galactooligosaccharide and polydextrose, wherein the prebiotic source is present in the nutritional composition in an amount of from 0.1 g/100 kcal to 1 g/100 kcal; and a protein source comprising whey and casein proteins, wherein the protein source is present in the nutritional composition in an amount of from 1 g/100 kcal to 5 g/100 kcal, further wherein the ratio of whey to casein proteins in the protein source is from 50:50 to 70:30 by weight and wherein the degree of hydrolysis of the whey and casein proteins included in the protein source is from 4% to 10%.

2. The method according to claim 1, wherein the probiotic source further comprises a probiotic selected from the group consisting of *Lactobacillus* species, *Bifidobacterium* species, *Bifidobacterium longum*, *Bifidobacterium animalis* subsp. *lactis* BB-12, and combinations thereof.

3. The method according to claim 1, wherein the child has a family history of allergies.

4. The method according to claim 1, wherein the degree of hydrolysis of the whey and casein proteins included in the protein source is from 6% to 9%.

5. The method according to claim 1, wherein the whey and casein proteins in the protein source have the following molecular weight distribution:

| Molar Mass (in Daltons) | % Molecular Weight Distribution |
| --- | --- |
| <500 | 11-20 |
| 500-1000 | 25-38 |
| 1000-2000 | 27-30 |
| 2000-3000 | 8-16 |
| 3000-5000 | 3-10 |
| >5000 | 2-11. |

6. The method according to claim 1, wherein the whey and casein proteins in the protein source have the following molecular weight distribution:

| Molar Mass (in Daltons) | % Molecular Weight Distribution |
| --- | --- |
| <500 | 17 |
| 500-1000 | 35.1 |
| 1000-2000 | 30.9 |
| 2000-3000 | 9.6 |
| 3000-5000 | 4.2 |
| >5000 | 2.8. |

7. The method of claim 1, wherein the nutritional composition further comprises TGF-β.

8. The method of claim 1, wherein the child was born as a preterm infant.

9. The method of claim 1, wherein the nutritional composition is an infant formula.

10. The method of claim 1, wherein the child has a family history of allergies.

11. A method of inducing oral tolerance in a child having an allergic reaction to at least one antigen, wherein the child is at least two years of age or older, the method comprising the steps of:
   exposing the child, when the child is an infant, to the at least one antigen, wherein the at least one antigen is selected from the group consisting of cow's milk, egg, soy, house dust, and mites; and
   administering to the child, when the child is an infant, a nutritional composition comprising
   from 3 g/100 kcal to 7 g/100 kcal of a fat or lipid source;
   from 8 g/100 kcal to 12 g/100 kcal of a carbohydrate source, wherein the carbohydrate source comprises between 15% and 55% lactose by weight;
   a probiotic source comprising *Lactobacillus rhamnosus* GG;
   a non-human lactoferrin;
   a prebiotic source comprising galactooligosaccharide and polydextrose, wherein the prebiotic source is present in the nutritional composition in an amount of from 0.1 g/100 kcal to 1 g/100 kcal; and a
   protein source comprising whey and casein proteins, wherein the protein source is present in the nutritional composition in an amount of from 1 g/100 kcal to 5 g/100 kcal, further wherein the ratio of whey to casein proteins in the protein source is from 50:50 to 70:30 by weight and wherein the degree of hydrolysis of the whey and casein proteins included in the protein source is from 4% to 10%.

12. The method according to claim 11, wherein the probiotic source further comprises a probiotic selected from the group consisting of *Lactobacillus* species, *Bifidobacterium* species, *Bifidobacterium longum*, *Bifidobacterium animalis* subsp. *lactis* BB-12, and combinations thereof.

13. The method according to claim 11, wherein the child has a family history of allergies.

14. The method according to claim 11, wherein the degree of hydrolysis of the whey and casein proteins included in the protein source is from 6% to 9%.

15. The method according to claim 11, wherein the whey and casein proteins in the protein source have the following molecular weight distribution:

| Molar Mass (in Daltons) | % Molecular Weight Distribution |
| --- | --- |
| <500 | 11-20 |
| 500-1000 | 25-38 |
| 1000-2000 | 27-30 |
| 2000-3000 | 8-16 |
| 3000-5000 | 3-10 |
| >5000 | 2-11. |

16. The method according to claim 11, wherein the whey and casein proteins in the protein source have the following molecular weight distribution:

| Molar Mass (in Daltons) | % Molecular Weight Distribution |
| --- | --- |
| <500 | 17 |
| 500-1000 | 35.1 |
| 1000-2000 | 30.9 |
| 2000-3000 | 9.6 |
| 3000-5000 | 4.2 |
| >5000 | 2.8. |

17. The method of claim 11, wherein the nutritional composition further comprises TGF-β.

18. The method of claim 11, wherein the child was born as a preterm infant.

19. The method of claim 11, wherein the nutritional composition is an infant formula.

20. A method of inducing oral tolerance in a child having an allergy to at least one antigen, wherein the child is at least two years of age or older, the method comprising the steps of:
  exposing the child, when the child is an infant, to the at least one antigen, wherein the at least one antigen is selected from the group consisting of cow's milk, egg, soy, house dust, and mites; and
  administering to the child, when the child is an infant, a nutritional composition comprising
    from 3 g/100 kcal to 7 g/100 kcal of a fat or lipid source;
    from 8 g/100 kcal to 12 g/100 kcal of a carbohydrate source, wherein the carbohydrate source comprises between 15% and 55% lactose by weight;
    a probiotic source comprising *Lactobacillus rhamnosus* GG;
    lactoferrin from a non-human source;
    a prebiotic source comprising galactooligosaccharide and polydextrose, wherein the prebiotic source is present in the nutritional composition in an amount of from 0.1 g/100 kcal to 1 g/100 kcal; and a
    protein source comprising whey and casein proteins, wherein the protein source is present in the nutritional composition in an amount of from 1 g/100 kcal to 5 g/100 kcal, further wherein the ratio of whey to casein proteins in the protein source is from 50:50 to 70:30 by weight and wherein the degree of hydrolysis of the whey and casein proteins included in the protein source is from 4% to 10%; and
  subsequently exposing the child to the at least one antigen.

* * * * *

```
                              SEQUENCE LISTING

<160> NUMBER OF SEQ ID NOS: 4

<210> SEQ ID NO 1
    <211> LENGTH: 4
    <212> TYPE: PRT
    <213> ORGANISM: Homo sapiens

<400> SEQUENCE: 1

Arg Arg Arg Arg
    1

<210> SEQ ID NO 2
    <211> LENGTH: 4
    <212> TYPE: PRT
    <213> ORGANISM: Homo sapiens

<400> SEQUENCE: 2

Arg Lys Val Arg
    1

<210> SEQ ID NO 3
    <211> LENGTH: 26
    <212> TYPE: PRT
    <213> ORGANISM: Homo sapiens

<400> SEQUENCE: 3

Phe Lys Cys Arg Arg Trp Gln Trp Arg Met Lys Lys Leu Gly Ala Pro
    1               5                   10                  15

Ser Ile Thr Cys Val Arg Arg Ala Phe Ala
                20                  25

<210> SEQ ID NO 4
    <211> LENGTH: 16
    <212> TYPE: PRT
    <213> ORGANISM: Homo sapiens

<400> SEQUENCE: 4

Ala Val Gly Glu Gln Glu Leu Arg Lys Cys Asn Gln Trp Ser Gly Leu
    1               5                   10                  15
```